United States Patent [19]
Kikuchi et al.

[11] Patent Number: 5,246,945
[45] Date of Patent: Sep. 21, 1993

[54] PIPERIDINE DERIVATIVES

[75] Inventors: Haruhiko Kikuchi, Tsurugashima; Hiroaki Satoh, Saitama; Toshio Suguro, Komoro; Koichiro Hagihara, Saitama; Toru Hayakawa, Kawagoe; Setsuko Mino, Fujimi, all of Japan

[73] Assignee: Nisshin Flour Milling Co., Ltd., Tokyo, Japan

[21] Appl. No.: 830,853

[22] Filed: Feb. 4, 1992

[30] Foreign Application Priority Data

Feb. 20, 1991 [JP] Japan .................... 3-045632

[51] Int. Cl.$^5$ .............. C07D 211/34; C07D 215/12; A61K 31/445
[52] U.S. Cl. .................... 514/331; 514/300; 514/317; 514/323; 514/326; 546/121; 546/168; 546/199; 546/200; 546/201; 546/209; 546/232; 546/233; 546/238; 546/239
[58] Field of Search .............. 546/121, 238, 168, 239, 546/199, 200, 201, 209, 233, 232; 514/323, 300, 326, 331, 317

[56] References Cited

U.S. PATENT DOCUMENTS

| | | | |
|---|---|---|---|
| 3,342,826 | 9/1967 | Miller | 546/233 |
| 4,310,532 | 6/1982 | Roll | 514/331 |
| 4,486,441 | 12/1984 | Fozard et al. | 424/265 |
| 4,563,465 | 6/1986 | Fozard et al. | 514/304 |
| 4,789,673 | 12/1988 | Donatsch et al. | 514/214 |
| 4,803,199 | 2/1989 | Donatsch et al. | 514/214 |
| 4,910,207 | 3/1990 | Donatsch et al. | 514/305 |
| 4,942,169 | 7/1990 | Sugimoto et al. | 546/204 |

FOREIGN PATENT DOCUMENTS

| | | |
|---|---|---|
| 0297651 | 1/1989 | European Pat. Off. |
| 0307145 | 3/1989 | European Pat. Off. |
| 0309423 | 3/1989 | European Pat. Off. |
| 0429984 | 6/1991 | European Pat. Off. |
| 2155927 | 5/1973 | France |
| WO85/02847 | 7/1985 | PCT Int'l Appl. |
| 1500105 | 2/1978 | United Kingdom |
| 2152049 | 7/1985 | United Kingdom |
| 2193633 | 2/1988 | United Kingdom |

OTHER PUBLICATIONS

Dudas "Derivatives of Piperidine Carbinols" CA 55: 11408i (1961).
Lepetit "Dihydrostreptomycin Salts" CA 56: 14246f (1962).
Schultz "Mechanism of Local Anesthetic Action" CA 74: 76285v (1971).
Hirata et al. "Benzoic Acids" CA 82: 31154a (1975).
The Lancet, Jun. 27, 1987, pp. 1461-1463. vol. 1, No. 8548 "Prevention of Emesis in Patients Receiving Cytotoxic Drugs by GR380321F, A ... " Cunningham, D. et al.
The New England Journal of Medicine, vo. 305, Oct. 15, 1981, pp. 905-909. Gralla, R. J. et al: "Antiemetic Efficacy of High-Dose Metoclopramide: Randomized Trials With Placebo and ... ".

Primary Examiner—C. Warren Ivy
Assistant Examiner—Celia Chang
Attorney, Agent, or Firm—Oblon, Spivak, McClelland, Maier & Neustadt

[57] ABSTRACT

Disclosed are compounds of formula (I)

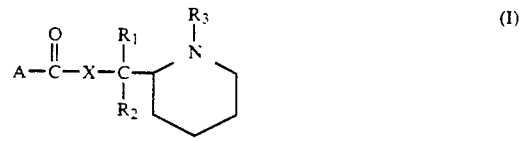

in which A is (a)

(b)

(Abstract continued on next page.)

-continued
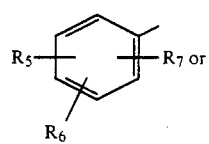
(e)
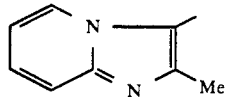
(c)
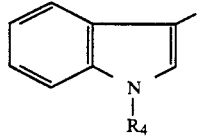
(f)
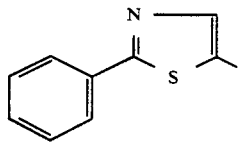
(d)
The compounds are selective antagonists of 5HT at 5-HT$_3$ receptors and useful in the treatment of psychotic disorders, neurotic diseases, gastric stasis symptoms, gastrointestinal disorders, nausea and vomiting.
4 Claims, No Drawings

PIPERIDINE DERIVATIVES

FIELD OF THE INVENTION

This invention relates to piperidine derivatives, to processes for their preparation and to pharmaceutical compositions comprising them.

In particular the invention relates to compounds which are selective antagonists of 5-hydroxytryptamine (5-HT) at 5-HT$_3$ receptors.

BACKGROUND OF THE INVENTION

Nausea and vomiting are serious problems frequently observed in patients receiving a cancer chemotherapeutic agent and radiotherapy, and control of the nausea and vomiting is a very important auxiliary treatment for undergoing satisfactory treatment for cancer. Since it is reported that intravenous administration of high-dose metoclopramide is effective in inhibition of the vomiting (Gralla, R. J. et al., N. Engl. J. Med. 305, 905-909 (1981)), the vomiting has better, though not perfectly, been controlled. However, it has been revealed that presently available antiemetics, particularly compounds containing a benzamide structure, are associated with adverse reactions such as sedation, ataxia, diarrhea and tasikinesia due to their dopamine-blocking activities and central nerve-depressant activities.

Specific antagonists of 5-HT$_3$ receptors which have recently been reported to inhibit vomiting induced during cancer chemotherapy (Cunningham, D. et al., The Lancet, 1, 1461-1463 (1987)) are considered as a potent antiemetic ones without adverse reactions associated.

Compounds having antagonists activity at 5-HT$_3$ receptors have been described previously. For example U.S. Pat. Nos. 4,486,441; 4,563,465; 4,789,673; 4,803,199 and 4,910,207; UK Patent Specification No. 2152049A and European Patent Specification No. 0309423A2 disclose compounds containing an azabicyclic moiety structure and European Patent Specifications Nos. 0297651A1 and 0307145A1 disclose compounds containing an imidazole ring structure.

Under such circumstances it has been desired to develop selective antagonists of 5-HT at 5-HT$_3$ receptors.

DETAILED DESCRIPTION OF THE INVENTION

We have now found new compounds which differ in structure from the prior compounds and possess a selectively effective antagonism against the effect of 5-HT at 5-HT$_3$ receptors.

According to one aspect of the invention, there are provided compounds of formula (I)

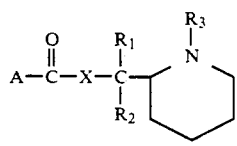

(I)

in which A represents a group selected from the following formulas (a) to (f)

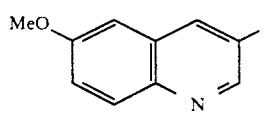

(a)

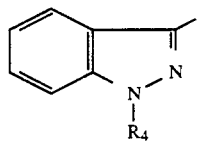

(b)

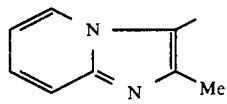

(c)

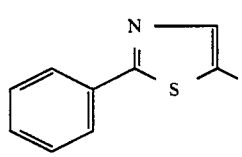

(d)

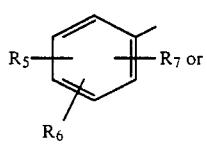

(e)

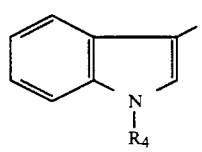

(f)

wherein R$_1$ and R$_2$ may be the same or different and each represents a hydrogen atom, a C$_1$-C$_6$ alkyl group, a phenyl group or an aryl (C$_1$-C$_4$) alkyl group, R$_3$ represents a C$_1$-C$_6$ alkyl group, R$_4$ represents a hydrogen atom, a C$_1$-C$_6$ alkyl group, a phenyl group or an aryl(-C$_1$-C$_4$)alkyl group, R$_5$, R$_6$ and R$_7$ may be the same or different and each represents a hydrogen atom, an amino group, a halogen atom, a C$_1$-C$_4$ alkoxy group or a phthalimide group and X represents O or NH, physiologically acceptable salts and quaternary ammonium salts thereof.

Suitable physiologically acceptable salts of the compounds of formula (I) include acid addition salts formed with organic or inorganic acids, for example, inorganic acid salts such as hydrochloride, hydrobromide, hydroiodide, sulfate and phosphate, and organic acid salts such as oxalate, maleate, fumarate, lactate, malate, citrate, tartrate, benzoate and methanesulfonate. The quaternary ammonium salts include those salts with a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p-toluenesulfonate. The compounds of formula (I) also include their N-oxide derivatives. Since the compounds of formula (I) and acid addition salts, quaternary ammonium salts and N-oxide derivatives thereof may exist in the form of a hydrate or a solvate, such hydrates and solvates are also included within the scope of the invention.

Compounds of formula (I) that contain at least one asymmetric carbon atom can be present in several stereoisomers. Such stereoisomers and their mixtures and racemates are embraced by the invention.

Examples of the substituents represented by $R_1$, $R_2$ and $R_4$ in formula (I) include hydrogen, $C_1$-$C_6$ alkyl such as methyl, ethyl n-propyl. iso-propyl, n-butyl. iso-butyl. tert butyl, n pentyl and n-hexyl, phenyl, benzyl, phenethyl or phenylpropyl. Examples of $R_3$ include $C_1$-$C_6$ alkyl such as methyl, ethyl, n-propyl iso-propyl, n-butyl, iso-butyl, tert-butyl, n-pentyl and n-hexyl.

The following compounds illustrate the scope of the compounds of formula (I).

1-(1-Methyl-2-piperidyl)ethyl 1-methylindazole-3-carboxylate,

1-Methyl-2-piperidylmethyl 1-methylindazole-3-carboxylate,

1-Methyl-2-piperidylmethyl 3 methoxyquinoline 3-carboxylate,

1-Methyl-2-piperidylmethyl 2-methoxy-4-aminobenzoate, 1-(1-Methyl-2-piperidyl)ethyl 2-methoxy-4-aminobenzoate, 1-Methyl-2-piperidylmethyl 2-methoxy-4-amino-5-chlorobenzoate, 1-(1-Methyl-2-piperidyl)ethyl 2-methoxy-4-amino-5-chlorobenzoate, 1-(1-Methyl-2-piperidyl)ethyl 2-methoxy-4-phthalimidebenzoate, 1,1-Dimethyl-2-(1-methyl-3-indazolylcarboxymethyl)-piperidinium iodide, 1-(1-Methyl-2-piperidyl)ethyl 2-methylimidazo-[1,2-a]pyridine-3-carboxylate, 1-(1-Methyl-2-piperidyl)ethyl 2-phenyl-1,3-thiazole-5-carboxylate, 1-(1-Ethyl-2-piperidyl)ethyl indole-3-carboxamide, 1-Methyl-2-piperidylmethyl 6-methoxyquinoline-3-carboxylate.

The compounds of formula (I) can be prepared by a variety of processes, for instance by condensation of a carboxylic acid of formula (II)

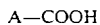

A—COOH     (II)

wherein A is as defined above or its reactive derivatives such as carboxylic acid halides, in particular carboxylic acid chloride, with a compound of formula (III)

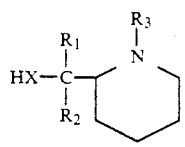

(III)

wherein $R_1$, $R_2$, $R_3$ and X are as defined above.

The reaction can be carried out under various conditions. For instance, the acid chloride of A—COOH is reacted with a compound of formula (III) in an organic solvent such as diethyl ether, diisopropyl ether, tetrahydrofuran, dimethoxyethane, 1,4-dioxane or dimethylformamide at a temperature in the range from $-20°$ C. to a boiling point of the solvent used, if needed in the presence of an inorganic or organic acid-binding agent such as triethylamine, tri-n butylamine, pyridine, dimethylaniline, tetramethylurea, metallic magnesium, n-butyllithium, lithium diisopropylamide, sodium amide, metallic sodium or sodium hydride. The desired product is obtained through extraction and purification steps following washing of the reaction mixture.

If the compound of formula (III) is a basic compound, this compound may be used in an excess amount for substitution of the acid-binding agent.

Alternatively, the compounds of formula (I) can be prepared by condensing the carboxylic acid of formula (II) or its reactive derivatives with a pyridine ring-containing compound corresponding to the compound of formula (III) and then hydrogenating the condensed product, thereby converting the pyridine ring to the piperidine ring.

Compounds of formula (I), which antagonise the effect of 5HT at 5-$HT_3$ receptors in the central nervous system, are useful in the treatment of conditions such as psychotic disorders (e.g., schizophrenia, mania, depression, anxiety, dementia, cognitive disorders, dependency on drugs, etc.) and neurotic diseases (e.g., migraine, etc.) or the like. Compounds of formula (I), which antagonise the effect of 5-HT at 5-$HT_3$ receptors in the peripheral nervous system, are useful in the treatment of gastric stasis symptoms of gastrointestinal dysfunction such as occur with dyspepsia, reflux oesophagitis, flatulence, and in the treatment of gastrointestinal disorders such as gastritis, peptic ulcer, diarrhea occurred by various causes, Hirschsprung's disease. Compounds of formula (I) are also useful in the treatment of nausea and vomiting, particularly that associated with cancer chemotherapy and radiotherapy.

According to another aspect of the invention, there is provided a pharmaceutical composition having a selective antagonism of 5-HT at 5-$HT_3$ receptors, which comprises as an active ingredient an effective amount of a compound of formula (I), its physiologically acceptable salt or quaternary ammonium salt. Such compositions may be formulated in conventional manner using one or more physiologically acceptable carriers and/or excipients.

The compounds of the invention can usually be administered orally or parenterally in the form of a pharmaceutical formulation. The pharmaceutical formulation includes tablets, capsules, suppositories, troches, syrup, cream, ointment, plasters, cataplasms, granules, powders, injection, suspension and the like. It may be in bilayered or multilayered tablet with other drugs. The tablet may also be coated with a conventional coating to form, for example, sugar-coated, enteric-coated or film-coated tablets.

In preparing the solid formulations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, glycerin, polyethylene glycol, stearic acid, magnesium stearate and talc are employed.

A vegetable or synthetic wax or fat or a similar base is used in preparing the semi-solid formulations.

As additives in preparing the liquid formulations are used, for example, sodium chloride, sorbitol, glycerin, olive oil, almond oil, propylene glycol and ethyl alcohol.

The active ingredient is contained in the formulation in an amount of 0.1–100% by weight, suitably 1–50% by weight in the case of formulations for oral administration and 0.1–10% by weight in the case of formulations for injection based upon the weight of the formulation.

Route and dosage of administration for the compounds of the invention are not specifically limited and are appropriately chosen depending upon form of the formulation, age and sex of the patient, severity of the disease and other factors. Daily dosage of the active ingredient is 1 ng–1000 mg.

The invention is further illustrated by the following examples.

EXAMPLE 1

1-(1-Methyl-2-piperidyl)ethyl
1-methylindazole-3-carboxylate

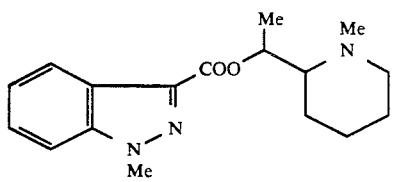

(1-Methyl-2-piperidyl)-1-ethanol (4.5 g, 31 mmol) was dissolved in dry THF (70 ml) and 1,3-dimethyl-2-imidazolidinone (20 ml) was added. The solution was ice-cooled and a hexane solution of n-BuLi (1.6M, 20 ml) was added dropwise. The reaction solution was stirred at room temperature for 20 minutes, to which was added dropwise a solution of 1 methylindazole-3-carboxylic acid chloride (5.4 g, 28 mmol) dissolved in a mixed solution of dry THF (70 ml) and 1,3-dimethyl-2-imidazolidinone (20 ml). The mixture was stirred overnight at room temperature, the reaction solution was concentrated under reduced pressure and a 5% sodium bicarbonate solution was added. It was extracted with chloroform. The organic layer was washed with a saturated sodium chloride solution and dried over anhydrous magnesium sulfate. The solvent was distilled off under reduced pressure to obtain a residue. Separation and purification of the residue by silica gel column chromatography (110 g SiO$_2$, chloroform:methanol=100:1) and further silica gel column chromatography with a different solvent (100 g SiO$_2$, hexane:ethyl acetate=1:1) gave the title compound, 0.52 g of a high polar isomer and 0.64 g of a low polar isomer, respectively.

Less polar isomer $^1$H-NMR δ(CDCl$_3$)1.10–1.38(m, 1 H), 1.43(d, J=7 Hz, 3 H), 1.50–1.68(m, 3 H), 1.72–1.97(m, 2 H), 2.07–2.22(m, 1 H), 2.25–2.32(m, 1 H), 2.36(s, 3 H), 2.82–2.97(m, 1 H), 4.17(s, 3 H), 5.66–5.79(m, 1 H), 7.33(dd, J=5 Hz, 1 H), 7.45(dd, J=1 Hz, 2 H), 8.18(d, J=8 Hz, 1 H);

IR(KBr) 2936, 2836, 2784, 1705, 1481, 1436, 1408, 1302, 1218, 1163, 1117, 772, 752cm$^{-1}$

More polar isomer
m.p. 71.5°–73° C.

$^1$H-NMR δ(CDCl$_3$) 1.25–1.38(m, 1 H), 1.45(d, J=7 Hz, 3 H), 1.51–1.65(m, 3 H), 1.79–1.92(m, 2 H), 2.03–2.20(m, 2 H), 2.40(s, 3 H), 2.82–2.98(m, 1 H), 4.17(s, 3 H), 5.50–5.64(m, 1 H), 7.32(dd, J=5 Hz, 1 H), 7.45(dd, J=1 Hz, 2 H), 8.22(dd, J=2 Hz, 1 H);

IR(KBr) 2942, 2848, 2770, 1718, 1480, 1435, 1410, 1201, 1171, 1161, 1117, 1090, 754 cm$^{-1}$

EXAMPLE 2

1-Methyl-2-piperidylmethyl
1-methylindazole-3-carboxylate

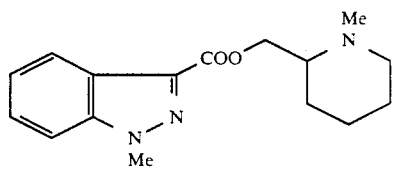

The title compound was prepared by the same procedure as in Example 1.

$^1$H-NMR δ(CDCl$_3$)1.25–1.95(m, 6 H), 2.05–2.40(m, 2 H), 2.42(s, 3 H), 1.83–2.95(m, 1 H), 4.18(s, 3 H), 4.45(dd, J=5 Hz, J=11 Hz, 1 H), 4.57(dd, J=1 Hz, J=11 Hz, 1 H), 7.27–7.50(m, 3 H), 8.24(d, J=8 Hz, 1 H);

MS(m/z) 2.88, 158, 112, 99, 70

EXAMPLE 3

1-Methyl-2-piperidylmethyl 3-methoxyquinoline
3-carboxylate

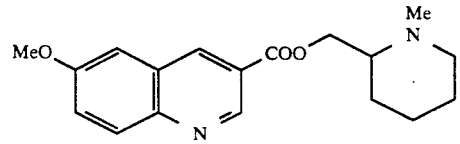

The title compound was prepared by the same procedure as in Example 1.

$^1$H-NMR δ(CDCl$_3$)1.20–2.07(m, 6 H), 2.07–2.39(m, 2 H), 2.43(s, 3 H), 2.85–2.97(m, 1 H), 3.96(s, 3 H), 4.47(d, J=5 Hz, 2 H), 7.18(d, J=2 Ha, 1 H), 7.48(dd, J=2 Ha, J=9 Ha, 1 H), 8.05(d, J=9 Ha, 1 H), 8.74(d, J=2 Hz, 1 H), 9.31(d, j=2 Hz, 1 H);

MS(m/z) 315, 186, 158, 99, 98, 70

EXAMPLE 4

1-Methyl-2-piperidylmethyl
2-methoxy-4-aminobenzoate

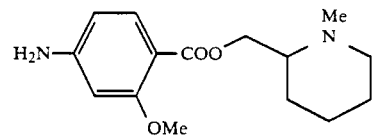

The title compound was prepared by the same procedure as in Example 1.

$^1$H-NWR δ(CDCl$_3$) 1.20–1.90(m, 5 H), 2.14–2.33(m, 3 H), 2.39(s, 3 H), 2.78–2.95(m, 1 H), 3.85(s, 3 H), 3.93–4.17(br., 2 H), 4.27(dd, J=5 Hz, J=12 Hz, 1 H), 4.33(dd, J=5 Hz, J=12 Hz, 1 H), 6.18–6.27(m, 2 H), 7.75(d, J=8 Hz, 1 H);

IR(KBr) 3470, 3370, 1690, 1610, 1255 cm=$^1$

EXAMPLE 5

1-(1-Methyl-2-piperidyl)ethyl
2-methoxy-4-aminobenzoate

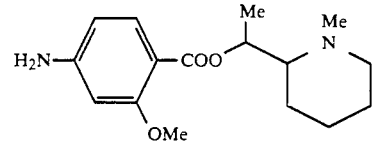

The title compound was prepared by the same procedure as in Example 1.

Less polar isomer
$^1$H-NMR δ(CDCl$_3$) 1.27(d, J=7 Hz, 3 H), 1.30–1.65(m, 2 H), 1.65–1.92(m, 2 H), 2.03–2.21(m, 2 H), 2.30(s, 3 H), 2.84(br. d, 1 H), 3.85(s, 3 H), 4.07(br. s, 2 H), 5.98(m, 1 H), 6.19(s, 1 H), 6.22(d, J=8 Hz, 1 H), 7.72(d, J=8 Hz, 1 H);

IR(film) 3460, 3365, 3250, 2945, 1692, 1610, 1470, 1350, 1242, 1210, 1150, 1078cm$^{-1}$ More polar isomer $^1$H-NMR δ(CDCl$_3$) 1.32(d, J=7 Hz, 3 H), 1.40–1.68(br., 2 H), 1.68–1.86(br, 2 H), 2.03–2.17(m, 2 H), 2.39(s, 3 H), 2.93(br. d, 1 H), 3.81(s, 3 H), 4.17(br. 2 H), 5.30(dd, J=5 Hz, J'=2 Hz, 1 H), 6.16(s, 1 H), 1.18(d, J=8 Hz, 1 H), 7.72(d, J=8 Hz, 1 H);

IR(film) 3448, 3350, 3225, 2940, 2850, 2785, 1690, 1608, 1465, 1280, 1250, 1150, 1078 cm$^{-1}$

EXAMPLE 6

1-Methyl-2-piperidylmethyl 2-methoxy-4-amino-5-chlorobenzoate

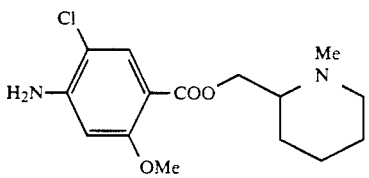

The title compound was prepared by the same procedure as in Example 1.

$^1$H-NMR δ(CDCl$_3$) 1.22–1.90(m, 6 H), 2.00–2.30(m, 2 H), 2.37(s, 3 H), 2.76–2.91(m, 1 H), 3.84(s, 3 H), 4.26(dd, J=5 Hz, JΔ=11 Hz, 1 H), 4.32(dd, J=5 Hz, J'=11 Hz, 1 H), 4.25–4.55(br., 2 H), 6.28(s, 1 H), 7.82(s, 1 H); MS(m/z) 313, 184, 113, 100, 70

EXAMPLE 7

(1-Methyl-Z-piperidyl)ethyl 2-methoxy-4 amino-5-chlorobenzoate

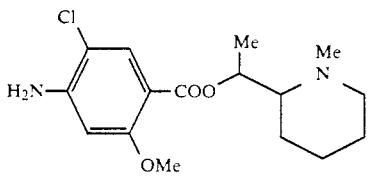

The title compound was prepared by the same procedure as in Example 1.

Less polar isomer $^1$H-NMR δ(CDCl$_3$) 1.28(d, J=6 Hz, 3 H), 1.30–1.88(m, 6 H), 2.03–2.24(m, 2 H), 2.31(s, 3 H), 2.81–2.93(m, 1 H), 3.85(s, 3 H), 4.35–4.52(br., 2 H), 5.41–5.57(m, 1 H), 6.29(s, 1 H), 7.80(s, 1 H)

More polar isomer $^1$H-NMR δ(CDCl$_3$) 1.32(d, J=6 Hz, 3 H) 1.40–1.93(m, 6 H), 1.93–2.17(m, 3 H), 2.37(s, 3 H), 2.83–2.98(m, 1 H), 3.83(s, 3 H), 4.28–4.52(br., 2 H), 5.23–5.38(m, 1 H), 7.26(s, 1 H), 7.82(s, 1 H)

EXAMPLE 8

1-(1-Methyl-2-piperidyl)ethyl 2-methoxy-4-phthalimide-benzoate

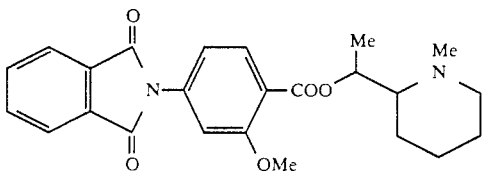

The title compound was prepared by the same procedure as in Example 1.

$^1$H-NMR δ(CDCl$_3$) 1.32(d, J=7 Hz, 3 H), 1.35–1.68(m, 4 H), 1.81(br., 2 H), 2.04–2.22(m, 2 H), 2.33(s, 3 H), 2.78–2.93(m, 1 H), 3.94(s, 3 H), 5.57(m, 1 H), 7.12–7.20(m, 2 H), 7.78–7.88(m, 2 H), 7.82–8.01(m, 3 H);

IR(film) 2935, 1722, 1610, 1379, 1255, 1082, 1030 cm$^{-1}$

EXAMPLE 9

1,1-Dimethyl-2-(1-methyl-3-indazolylcarboxymethyl)-piperidinium iodide

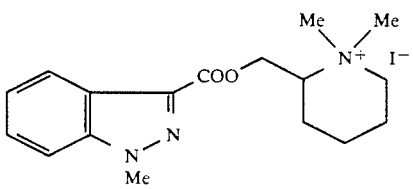

0.5 g (1.8 mmol) of 1-methyl-2-piperidylmethyl 1-methylindazole-3-carboxylate obtained in Example 2 was dissolved in toluene (5 ml), methyl iodide (1 ml) was added at room temperature with stirring and the mixture was stirred for one hour. After it was confirmed by thin layer chromatography that the spot of 1-methyl 2-piperidylmethyl 1-methylindazole-3-carboxylate disappeared, a precipitating crystal was collected by filtration. The crystal was washed with small amounts of toluene and dried under reduced pressure at room temperature to afford 0.49 g (1.2 mmol) of the quaternary ammonium salt of the title compound.

$^1$H-NMR δ(D$_2$O) 1.60–2.20(m, 6 H), 3.21(s, 3 H), 3.36(s, 3 H), 3.45–3.65(m, 2 H), 3.80–4.10(m, 1 H), 4.03(s, 3 H), 4.6–5.5(br., 2 H), 7.30–7.45(m, 1 H), 7.47–7.62(m, 2 H), 7.88(d, J=8 Hz, 1 H);

MS(m/z) 302, 185, 159, 145, 126, 93, 58

EXAMPLE 10

1-(1-Methyl-2-piperidyl)ethyl 2-methylimidazo-[1,2-a]pyridine-3-carboxylate

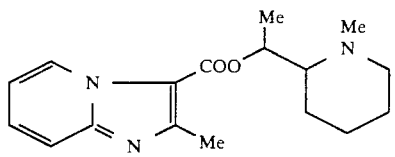

The title compound was prepared by the same procedure as in Example 1.

Less polar isomer $^1$H-NMR δ(CDCl$_3$) 1.38(d, J=7 Hz, 3 H), 1.20–2.00(m, 6 H), 2.00–2.33(m, 2 H), 2.36(s, 3 H), 2.73(s, 3 H), 2.84–2.97(m, 1 H), 5.58–5.73(m, 1 H), 6.99(t, J=7 Hz, 1 H), 7.39(dd, J=7 Hz, J=9 Hz, 1 H), 7.62(d, J=9 Hz, 1 H), 9.74(d, J=7 Hz, 1 H)

EXAMPLE 11

1-(1-(1-Methyl-2-piperidyl)ethyl 2-phenyl-1,3-thiazole-5-carboxylate

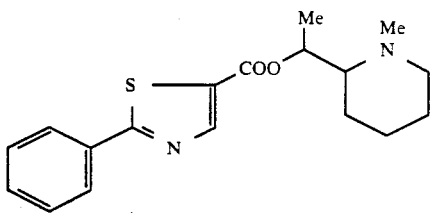

The title compound was prepared by the same procedure as in Example 1.

Less polar isomer $^1$H-NMR δ(CDCl$_3$) 1.36(d, J=7 Hz, 3 H), 1.20–1.94(m, 6 H), 2.02–2.30(m, 2 H), 2.33(s, 3 H), 2.83–2.96(m, 1 H), 5.50–5.66(m, 1 H), 7.41–7.52(m, 3 H), 7.97–8.07(m, 2 H), 8.11(m, 2 H);

More polar isomer $^1$H-NMR δ(CDCl$_3$) 1.39(d, J=6 Hz, 3 H), 1.20–1.95(m, 6 H), 2.01–2.18(m, 2 H), 2.40(s, 3 H), 2.36–2.49(m, 1 H), 5.38–5.52(m, 1 H), 7.40–7.51(m, 3 H), 7.94–8.07(m, 2 H), 8.11(s, 1 H)

EXAMPLE 12

1-(1-Methyl-2-piperidyl)ethyl indole-3-carboxamide

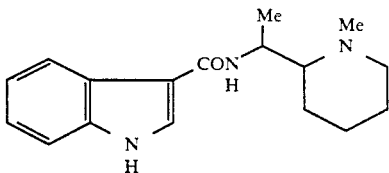

To a THF solution (300 ml) of 2-(1-aminoethyl)-pyridine (10.4 g, 85.1 mmol) was added dropwise a THF solution (100 ml) of indole-3-carboxylic acid chloride (24.0 g, 134 mmol) over a period of 30 minutes. The mixture was stirred at room temperature for 2 hrs. The reaction solution was diluted with ethyl acetate (300 ml), water (500 ml) was added and the mixture was stirred. The organic layer was separated and the water layer was made alkali with potassium hydroxide and extracted three times with ethyl acetate. The extract was washed with a saturated sodium chloride solution and dried over anhydrous magnesium sulfate. The solvent was concentrated under reduced pressure to obtain a residue. Separation and purification of the residue by silica gel column chromatography (300 g SiO$_2$, ethyl acetate) gave 1.04 g of 1-(2-pyridyl)ethyl indole-3-carboxamide as yellow oily product.

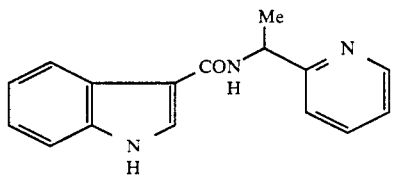

$^1$H-NMR δ(CDCl$_3$) 1.60(d, J=7 Hz, 3 H), 5.42(q, J=7 Hz, 1 H), 7.15–7.35(m, 5 H), 7.65(m, 2 H), 8.11(d, J=7 Hz, 1 H), 8.57(d, J=5 Hz, 1 H), 10.42(s, 1 H);
IR(film) 3186, 3056, 1624, 1205, 747cm$^{-1}$ The resulting 1-(2-pyridyl)ethyl indole-3-carboxamide (1.0 g. 3.8 mmol) and methyl iodide (5 ml) were mixed and the mixture was reacted at 100° C. in a stainless sealed tube for 3 hrs. The resulting quaternary ammonium salt was dissolved in methanol (100 ml) and water (10 ml) was added. To the mixture cooled to 0° C. was added slowly sodium borohydride (1.7 g, 45 mmol). After completion of the addition, the mixture was stirred at room temperature for 2 hrs. Methanol was distilled off under reduced pressure to obtain a residue. The residue mixed with water was extracted with chloroform. The extract was washed with a saturated sodium chloride solution and dried over anhydrous magnesium sulfate. The residue obtained by concentration under reduced pressure was separated by silica gel column chromatography (30 g SiO$_2$, chloroform). The tetrahydro form (1.0 g) obtained as yellow oily product was dissolved in ethanol (50 ml) and subjected to catalytic reduction (2.5 kg/cm$^2$ H$_2$) using a platinum oxide catalyst (80 mg). The catalyst was filtered and washed with ethanol. The filtrate was concentrated under reduced pressure. The resulting residue was separated and purified by silica gel column chromatography (30 g SiO$_2$, chloroform:methanol=9:1) to afford 0.10 g of the title compound as yellow oily product.

$^1$H-NMR δ(CDCl$_3$) 1.29(d, J=7 Hz, 3 H), 1.30–1.90(m, 8 H), 2.42(s, 3 H), 2.91(d, J=12 Hz, 1 H), 4.52(q, J=hz, 1 H), 6.69(d, J=7 Hz, 1 H), 7.22(m, 2 H), 7.42(m, 1 H), 7.86(s, 1 H), 8.00(m, 1 H), 10.38(s, 1 H)

The compounds prepared in the above examples were respectively tested for antagonism of 5-HT at 5-HT$_3$ receptors.

Administration of 5-HT (serotonin) to anesthesized rats via jugular vein induces temporary bradycardia (von Benzold Jarisch Reflex)(A.S. Paintal, Physiol. Rev., 53, 159-227 (1973)). It is demonstrated by Rechardson et al. (Nature, 316, 126-131 (1985)) that the 5-HT-induced reflex is produced via 5-HT$_3$ receptors. Accordingly, an effective and selective antagonism of 5-HT at 5-HT$_3$ receptors by a compound of the invention, if any, could be demonstrated by inhibition of said reflex.

Thus, rats were anesthesized with urethane (1 g/kg, i.p.) and recorded for blood pressure and heart rate from left femoral artery. Percent inhibition was calculated from bradycardia induced by 5-HT (30 μg/kg) given 5 min. following intrajugular administration of a compound of the invention, taking the bradycardia induced by the intrajugular administration of 5-HT. The percent inhibition is listed in the table below.

In this test, all of the test compounds were tested in the form of hydrochloride except for the compounds prepared in Example 9. Therefore, concentration of the test drug is expressed in terms of the concentration of the hydrochloride except for the compounds prepared in Example 9.

| Antagonism of 5-HT$_3$ | |
|---|---|
| Example No. | % Inhibition (100 μg/kg, i.v.) |
| 1 (less polar isomer) | 49 |
| 2 | 34 |
| 3 | 26 |
| 5 (more polar isomer) | 16 |
| 6 | 76 |
| 7 (less polar isomer) | 50 |
| 9 | 58 |

The following examples illustrate pharmaceutical formulations according to the invention.

| Tablets (per tablet) | |
| --- | --- |
| 1-(1-Methyl-2-piperidyl)ethyl 1-methylindazole-3-carboxylate (less polar isomer) | 10 mg |
| Lactose | 67 mg |
| Crystalline cellulose | 15 mg |
| Corn starch | 7 mg |
| Magnesium stearate | 1 mg |
| | 100 mg |

The above ingredients were uniformly blended to produce powders for direct compression. The powders were formed in a rotary tabletting machine to tablets each 6 mm in diameter and weighing 100 mg.

| Granules (per divided packet) | |
| --- | --- |
| 1-Methyl-2-piperidylmethyl 1-methylindazole-3-carboxylate | 10 mg |
| Lactose | 90 mg |
| Corn starch | 50 mg |
| Crystalline cellulose | 50 mg |
| Hydroxypropylcellulose | 10 mg |
| Ethanol | 9 mg |

The active ingredient, lactose, corn starch and crystalline cellulose were uniformly blended and a solution of hydroxypropylcellulose in ethanol was added. The mixture was kneaded and granulated by extrusion in a grade. The granules were then dried in a drier at 50° C. The dried granules were screened to granule sizes between 297 μm and 1460 μm to give a granule formulation weighting 200 mg per divided packet.

| Syrups | |
| --- | --- |
| 1-Methyl-2-piperidylmethyl 2-methoxy-4-amino-5-chlorobenzoate | 1.000 g |
| Refined sugar | 30.000 g |
| D-Sorbitol, 70 w/v % | 25.000 g |
| Ethyl paraoxybenzoate | 0.030 g |
| Propyl paraoxybenzoate | 0.015 g |
| Flavor | 0.200 g |
| Glycerin | 0.150 g |
| 96% Ethanol | 0.500 g |
| Distilled water | q.s. |
| To a total amount of | 100 ml |

Refined sugar, D-sorbitol, methyl paraoxybenzoate, propyl paraoxybenzoate and the active ingredient were dissolved in 60 g of warm water. After cooling, glycerin and a solution of the flavor in ethanol were added. To the mixture was then added water to 100 ml.

| Injections | |
| --- | --- |
| 1-(1-Methyl-2-piperidyl)ethyl 2-methoxy-4-amino-5-chlorobenzoate (less polar isomer) | 1 mg |
| Sodium chloride | 10 mg |
| Distilled water | q.s. |
| To a total amount of | 1.0 ml |

Sodium chloride and the active ingredient were dissolved in distilled water to give a solution in a total amount of 1.0 ml.

| Suppositories | |
| --- | --- |
| 1,1-Dimethyl-2-(1-methyl-3-indazolylcarboxymethyl)piperidinium iodide | 2 g |
| Polyethylene glycol 4000 | 20 g |
| Glycerin | 78 g |
| To a total amount of | 100 g |

Glycerin was added tot he active ingredient to give a solution. To the solution was added polyethylene glycol 4000, and the mixture was warmed to give a solution. The solution was poured into suppository mold and solidified by cooling to prepare suppositories each weighing 1.5 g.

What is claimed is:

1. A compound of formula (I)

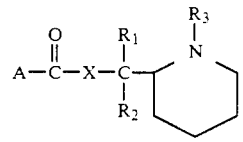

in which A represents

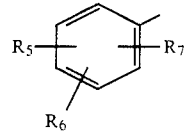

wherein $R_1$ and $R_2$ may be the same or different and each represents a hydrogen atom, a $C_1$-$C_6$ alkyl group, a phenyl group or a phenyl($C_1$-$C_4$)alkyl group provided that when either one of $R_1$ and $R_2$ is phenyl the other is not a hydrogen atom, $R_3$ represents a $C_1$-$C_6$ alkyl group, $R_5$ represents a $C_1$-$C_4$ alkoxy group, $R_6$ represents an amino or phthalimido group, $R_7$ represents a hydrogen or halogen atom and X represents oxygen, or a physiologically acceptable salt or quaternary ammonium salt thereof.

2. A compound of claim 1 where $R_1$ and $R_2$ are individually hydrogen or $C_1$-$C_4$ alkyl and $R_3$ is $C_1$-$C_4$ alkyl.

3. A pharmaceutical composition for use as a selective antagonist of 5-HT at 5-$HT_3$ receptors which comprises an effective amount of a compound of formula (I) as defined in claim 1 or a physiologically acceptable salt thereof together with at least one physiologically acceptable carrier or excipient.

4. A pharmaceutical composition of claim 3 wherein said physiologically acceptable salt is a quaternary ammonium salt.

* * * * *